(12) United States Patent
Wang

(10) Patent No.: US 8,152,355 B2
(45) Date of Patent: Apr. 10, 2012

(54) LAMP-SET STRUCTURE

(75) Inventor: Shao-Hua Wang, Taipei (TW)

(73) Assignees: Shao-Hua Wang, Taipei (TW); Ronald Leslie Ferguson, Elizabeth, CO (US); Brent Allen Safer, Elizabeth, CO (US)

( * ) Notice: Subject to any disclaimer, the term of this patent is extended or adjusted under 35 U.S.C. 154(b) by 360 days.

(21) Appl. No.: 12/620,340

(22) Filed: Nov. 17, 2009

(65) Prior Publication Data
US 2010/0181932 A1    Jul. 22, 2010

(30) Foreign Application Priority Data

Jan. 20, 2009   (CN) ...................... 2009 2 0129631 U

(51) Int. Cl.
*H01R 33/00* (2006.01)
(52) U.S. Cl. ........ 362/647; 362/657; 362/655; 362/658; 362/659; 362/646; 362/249.02; 315/313
(58) Field of Classification Search .................. 315/313, 315/297; 362/247
See application file for complete search history.

(56) References Cited

U.S. PATENT DOCUMENTS

| 8,002,432 B2* | 8/2011 | Chen et al. ..................... 359/802 |
| 2006/0262523 A1* | 11/2006 | Smith et al. ................... 362/157 |

* cited by examiner

*Primary Examiner* — Douglas W Owens
*Assistant Examiner* — Jonathan Cooper
(74) *Attorney, Agent, or Firm* — Muncy, Geissler, Olds & Lowe, PLLC

(57) ABSTRACT

The present invention includes a lamp cap and a lamp body. An interior of the lamp cap is provided with an illuminating element which is electrically connected with a circuit board. The circuit board is provided with electric contacts which are exposed at a bottom of the lamp cap and peripheries of the lamp cap are provided with latching parts. The lamp body includes a handheld part and a lamp holder. An interior of the lamp holder is provided with fastening parts which correspond with the latching parts of the lamp cap, allowing the lamp cap to be engaged on and electrically connected with the lamp holder. In addition, the handheld part is provided with a control switch.

18 Claims, 8 Drawing Sheets

LAMP-SET STRUCTURE

BACKGROUND OF THE INVENTION a) Field of the Invention

The present invention relates to a lamp-set structure, and more particularly to a lamp-set structure by which a lamp cap can not only be stably and electrically connected, but be dismantled and replaced, through mutual engagement and contact of lamp cap latching parts, electric contacts, lamp holder fastening parts and connection contacts.

b) Description of the Prior Art

As emerging of consciousness of environmental protection in recent years and at a same time for a purpose of saving energy and reducing emission of carbon dioxide, all kinds of innovated energy saving products have been developed. Especially for a lamp-set product, an LED (Light Emitting Diode) lamp-set product is further developed from a tungsten lamp in an early day to a fluorescent lamp. In addition to largely reducing electricity consumed by the lamp-set, this LED lamp-set product can more effectively extend a life time of usage of the lamp-set.

However, in the existing lamp-set structure, the lamp cap and the lamp body are normally formed integrally. Therefore, when an illuminating element (such as a light bulb or an LED) in the lamp cap is broken, a user is not able to replace, which largely increases a utilization cost and a procurement cost of the lamp-set.

On the other hand, in a technological field applying to a human face, one of major achievements in medical technology development uses light of different wavelength to irradiate on skin in order to achieve effects of caring skin and improving a skin quality. It is shown from many researches that a different effect will be resulted when light of different wavelength irradiates on a human body. Accordingly, all kinds of lamp-set products have shown up in markets, and as a cosmetic lamp-set which utilizes a principle of light irradiation to improve a facial quality of the human body can achieve a cosmetic function, it has been widely applied.

In the existing market, there is a lamp cap which is assembled by many LEDs of various wavelengths and is formed integrally with a handheld unit. Although this cosmetic tool can achieve the effect of improving the facial quality of the human body, the lamp cap cannot be dismantled and replaced as the handheld unit and the lamp cap are formed integrally, causing inconvenience in use of and increasing a cost of the lamp-set.

As a result, there are still a lot of shortcomings for the aforementioned conventional lamp-set, which is therefore, really not a perfect design and needs to be improved very much.

SUMMARY OF THE INVENTION

The primary object of the present invention is to provide a lamp-set structure wherein a lamp cap can be dismantled from a lamp body and replaced.

Another object of the present invention is to provide a lamp-set structure wherein a lamp cap and a lamp holder can be engaged robustly and can be electrically connected, through mutual engagement of lamp cap latching parts, lamp holder fastening parts and exposed electric contacts.

To achieve the aforementioned objects, the lamp-set structure of the present invention includes a lamp cap and a lamp body, wherein an interior of the lamp cap is accommodated with more than one illuminating element which is electrically connected with a circuit board, and the other end of the circuit board is provided with electric contacts which are exposed at a bottom of the lamp cap. Through the provision of the electric contacts, an electric source which is provided by the lamp body described below can be conducted on the circuit board, allowing the illuminating elements on the circuit board to illuminate. Peripheries of the lamp cap are provided with more than one latching part which can be a rectangular strip.

The lamp body includes a handheld part and a lamp holder. An interior of the lamp holder is provided with fastening parts which correspond with the latching parts of the lamp cap. Each fastening part can be an L-shaped locking slot, allowing each rectangular strip of the lamp cap to be latched and fixed with the lamp holder through the L-shaped locking slot. The lamp holder is provided with connection contacts which correspond with the electric contacts of the lamp cap. Through electric contact of the electric contacts with the connection contacts, electric energy on the lamp body can be transmitted to the lamp cap. There are three connection contacts described above, including a power supply contact, a grounding contact and a voltage detection contact by functions.

The handheld part of the lamp body is provided with a control switch to control on and off of the illuminating element of the lamp cap. Through the mutual engagement of the lamp cap latching parts, the lamp holder fastening parts, the exposed electric contacts and connection contacts, the lamp cap can not only be stably and electrically connected, but be dismantled and replaced.

To enable a further understanding of the said objectives and the technological methods of the invention herein, the brief description of the drawings below is followed by the detailed description of the preferred embodiments.

DETAILED DESCRIPTION OF THE PREFERRED EMBODIMENTS

Figure 1:
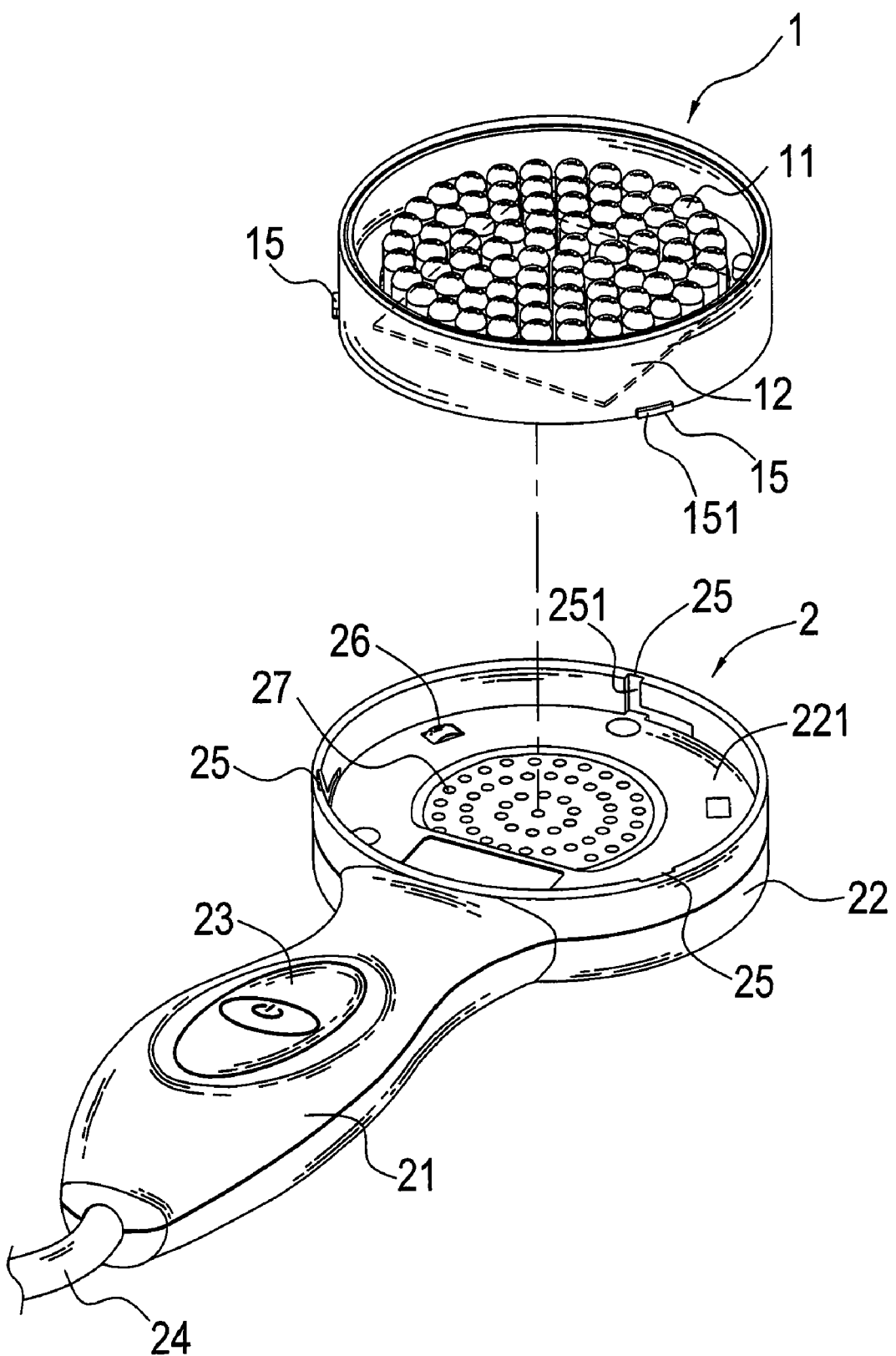
FIG. 1 shows a three-dimensional exploded view of a lamp-set structure of the present invention.
Figure 2:
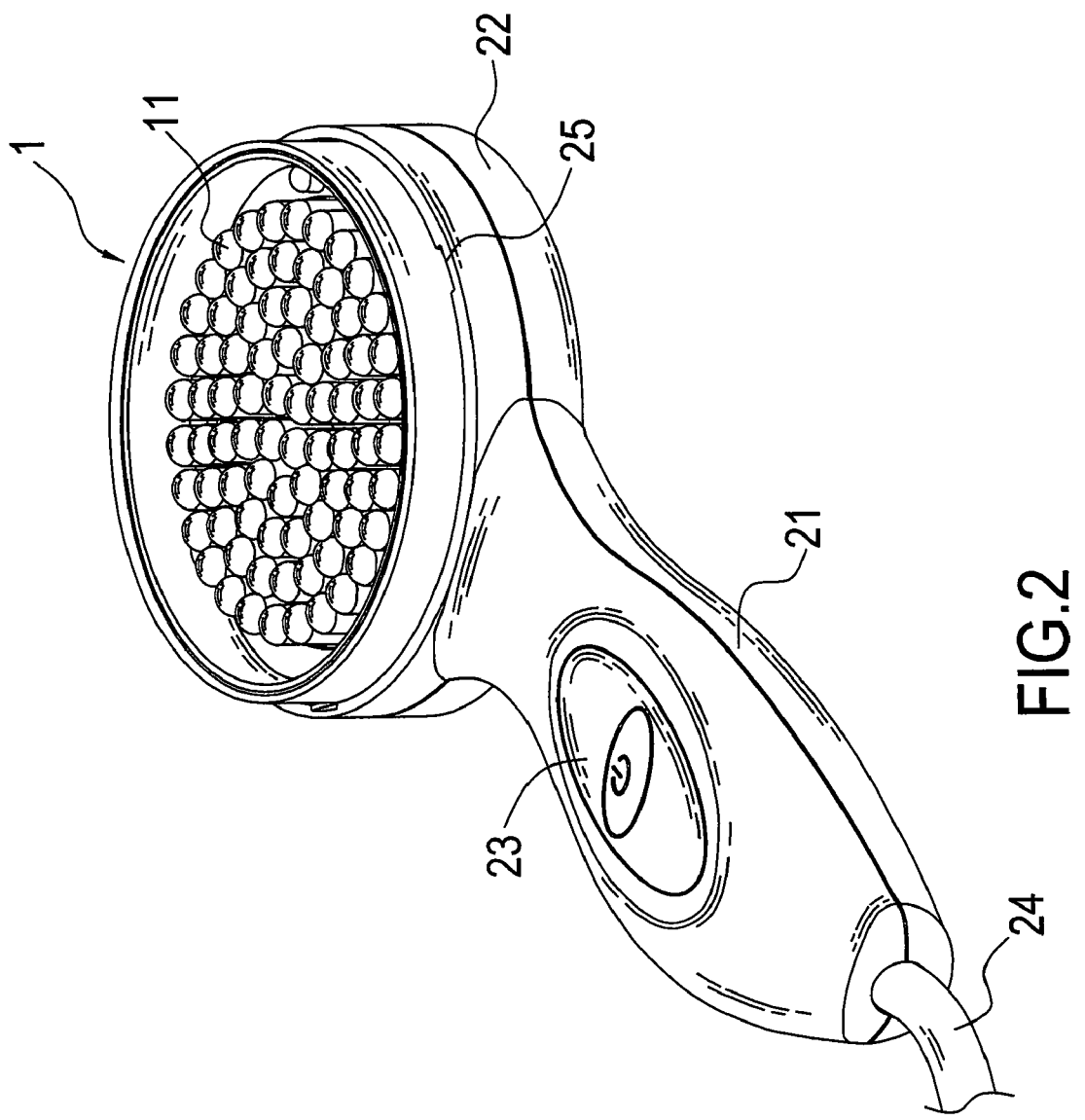
FIG. 2 shows a three-dimensional perspective view of a lamp-set structure of the present invention.
Figure 3:
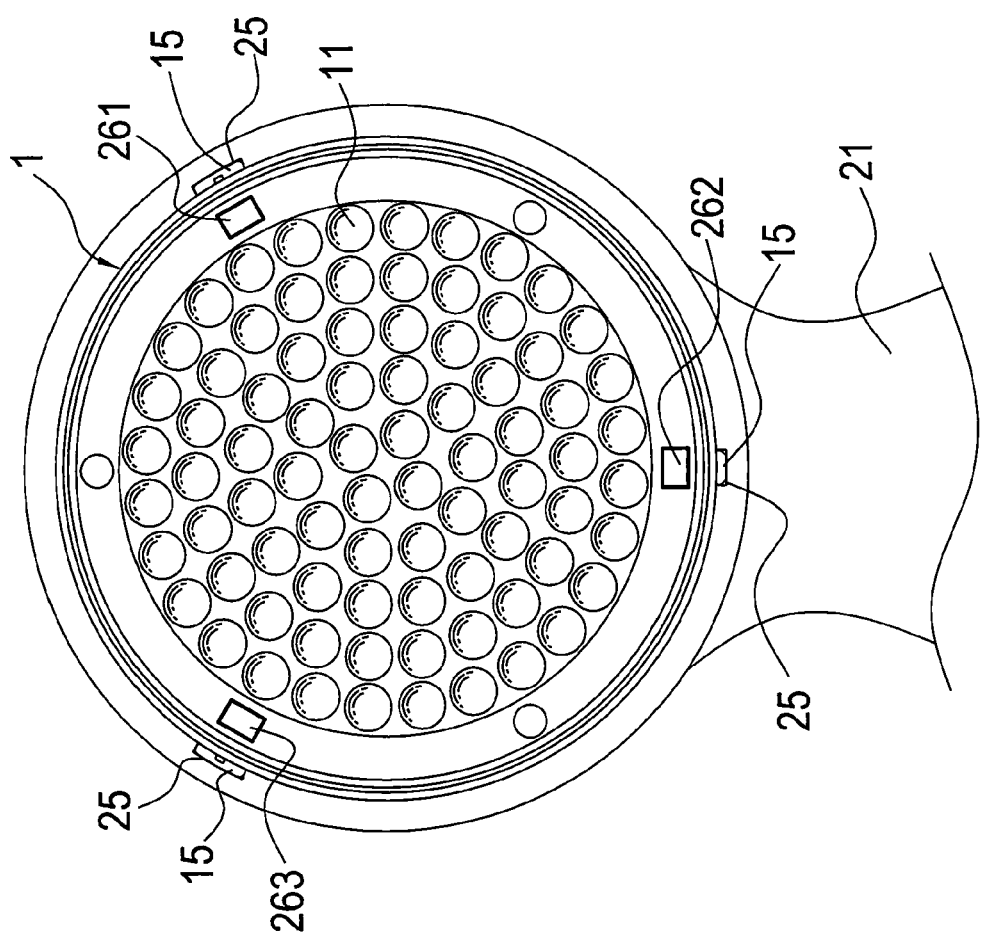
FIG. 3 shows a top view of a lamp body of a lamp-set structure of the present invention.
Figure 4:
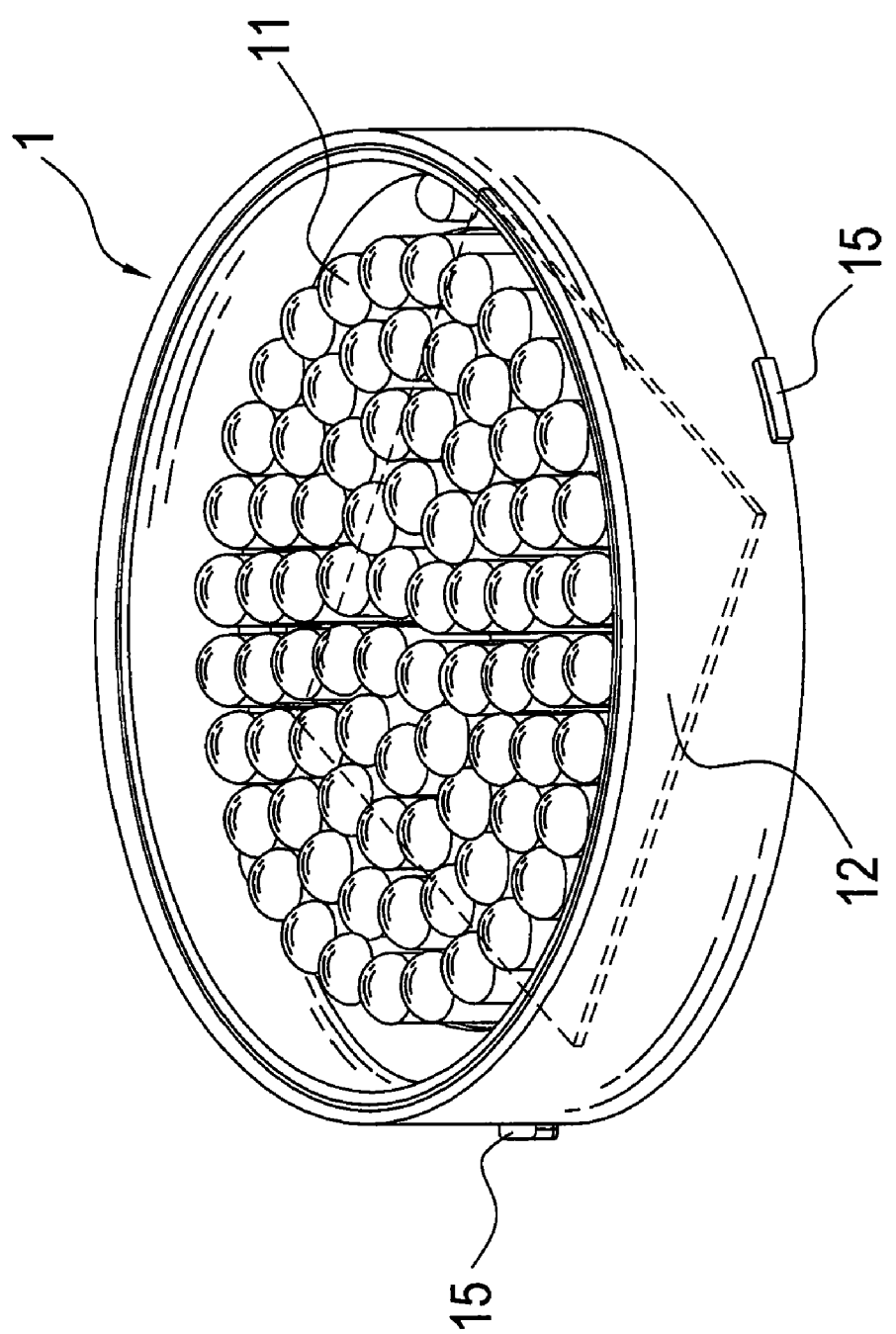
FIG. 4 shows a three-dimensional schematic view of a lamp body of a lamp-set structure of the present invention.
Figure 5:
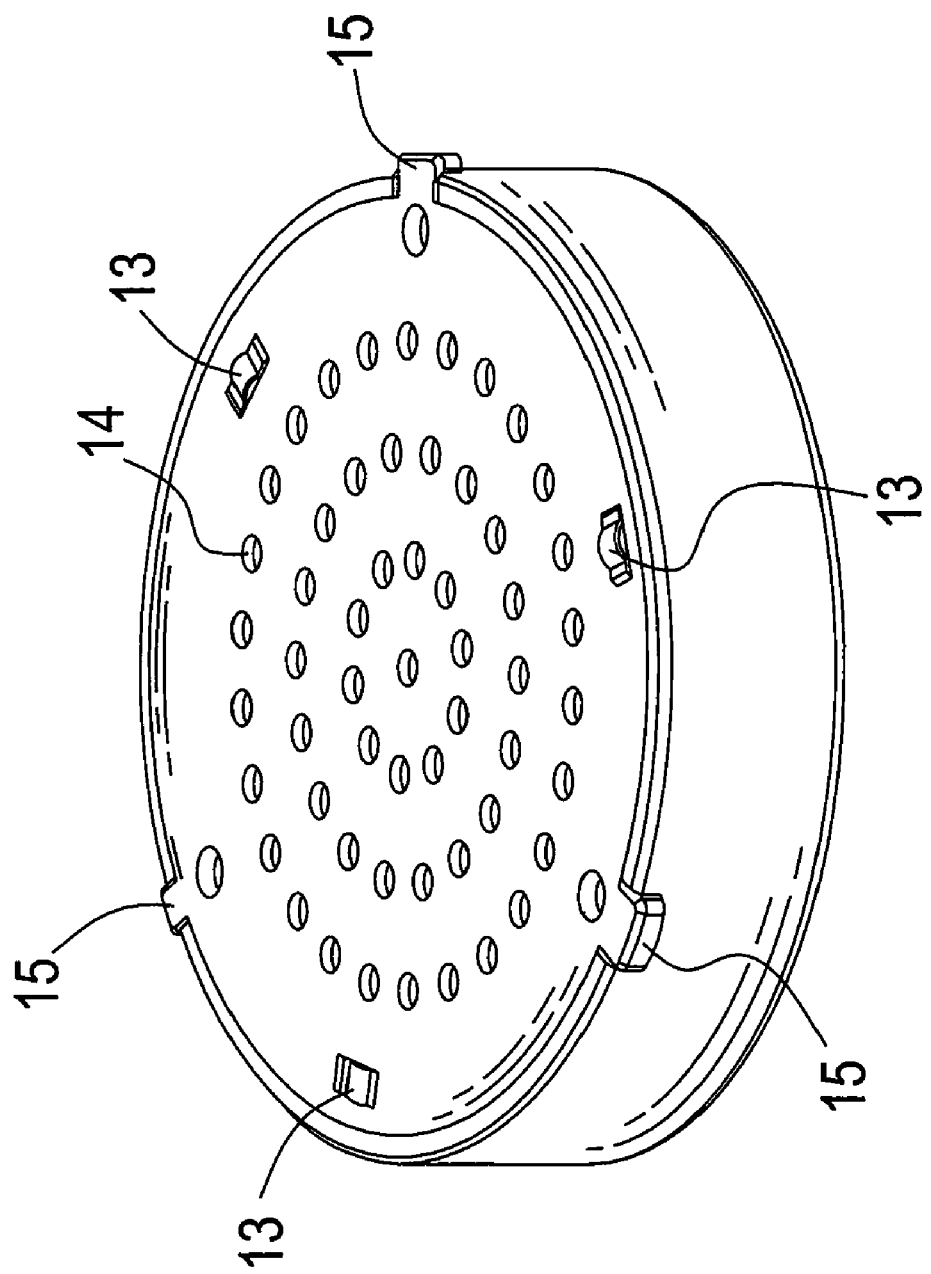
FIG. 5 shows a three-dimensional view of another angle of a lamp body of a lamp-set structure of the present invention.
Figure 6:
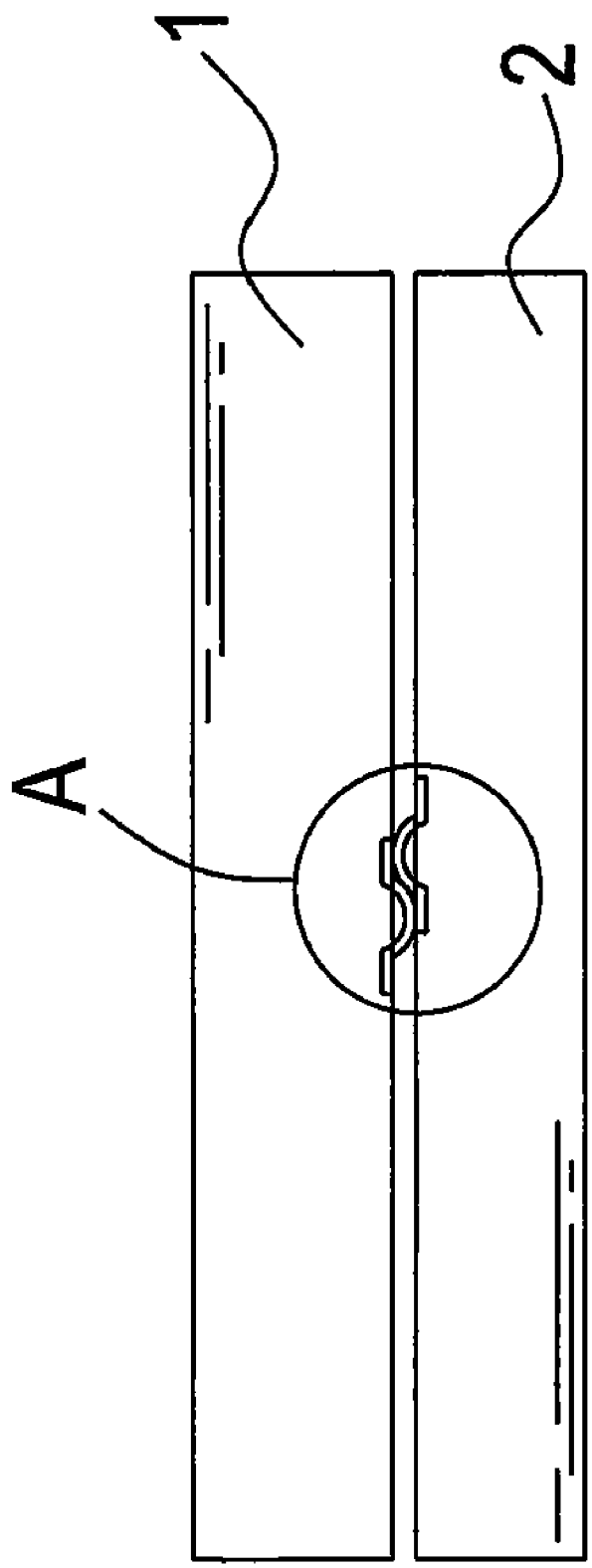
FIG. 6 shows a schematic view of electric contacts and connection contacts of a lamp-set structure of the present invention.
Figure 6A:
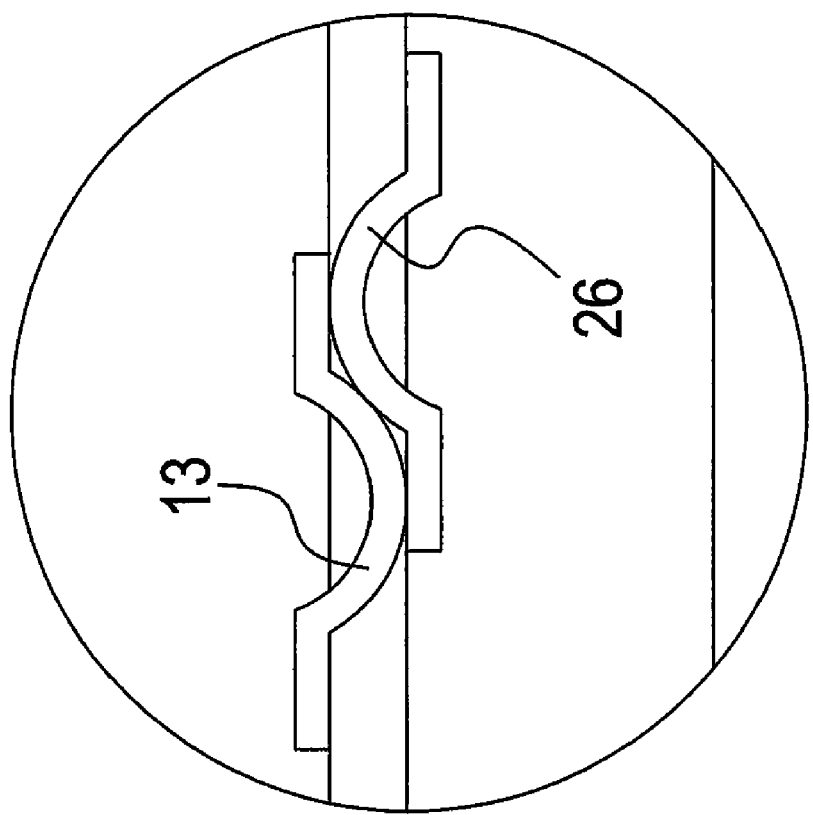
FIG. 6A shows an exploded view of electric contacts and connection contacts of a lamp-set structure of the present invention.
Figure 7:
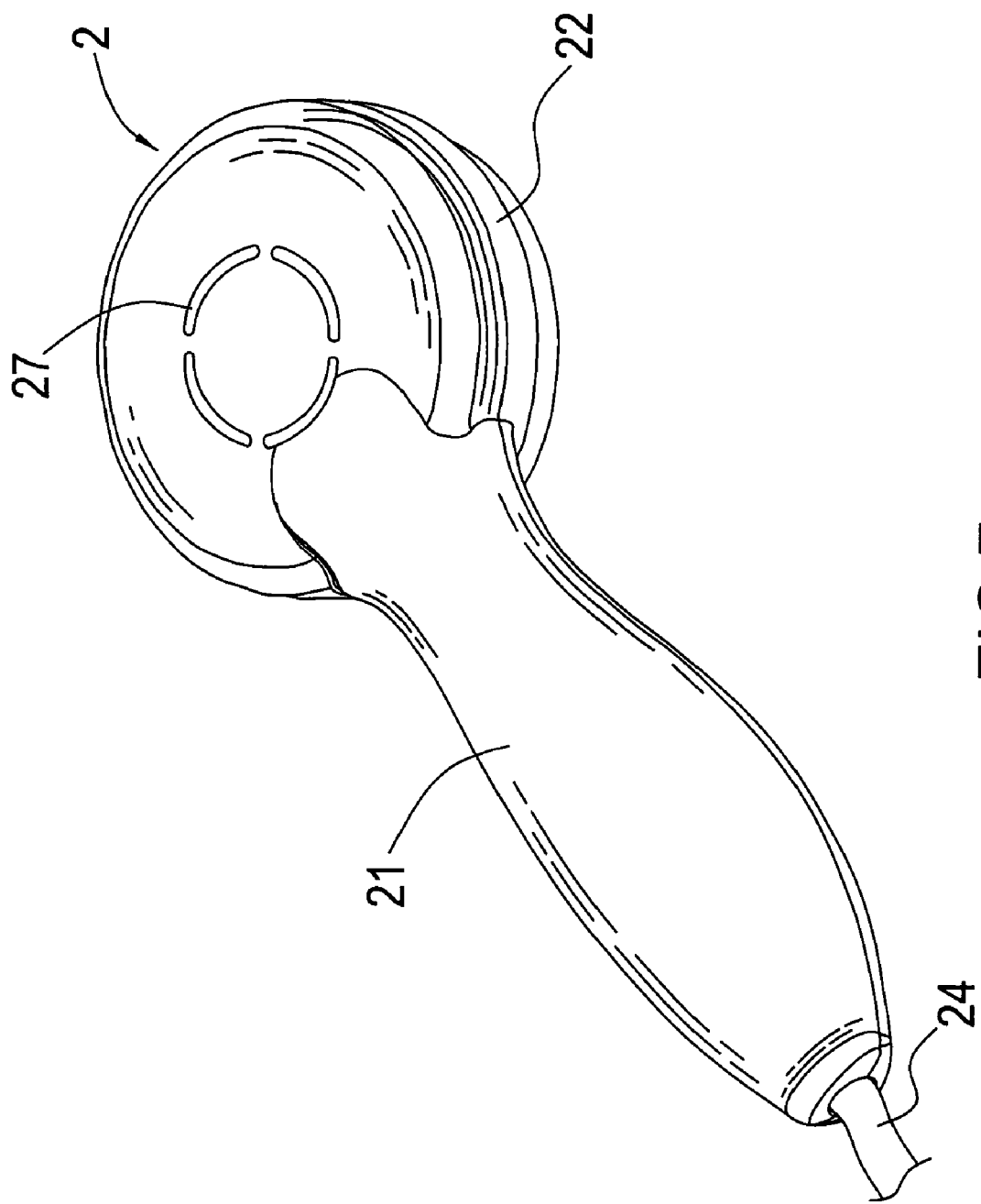
FIG. 7 shows a three-dimensional schematic view of a rear side of a lamp-set structure of the present invention.

Referring to FIGS. 1 to 7, it shows a three-dimensional exploded view, a three-dimensional perspective view and three-dimensional schematic views of a lamp-set structure of the present invention. The lamp-set structure of the present invention comprises a lamp cap 1, an interior of which is accommodated with more than one illuminating element 11 which can be an LED, is provided on a circuit board 12 and is electrically connected with the circuit board 12. The other end of the circuit board 12 is provided with more than two electric contacts 13 which are exposed at a bottom of the lamp cap 1. The electric contacts 13 are elastic and arc-shaped units and through the provision of the electric contacts 13, an electric source can be conducted on the circuit board 12, allowing the illuminating elements 11 on the circuit board 12 to illuminate. The bottom of the lamp cap 1 is provided with more than one heat dissipation hole 14 through which heat generated by the illuminating elements 11 and the circuit board 12 due to illumination can be dissipated, thereby extending a lifetime of usage of the illuminating elements 11 and the circuit board 12. Peripheries of the lamp cap 1 are provided with latching parts 15 which can be rectangular strips 151 and can be latched and connected with fastening parts of a lamp body 2, as described below. In the present embodiment, there are three latching parts 15, two large and one small, which are fitted with the fastening parts 25 of the lamp body 2 described below.

The lamp-set structure also includes the lamp body 2 which is constituted by a handheld part 21 and a lamp holder 22. The handheld part 21 is an ergonomic structure for holding and is provided with a control switch 23. The other end of the lamp body 2 is, on the other hand, extended with a power cord 24 to provide electricity to the lamp body 2 and the lamp cap 1. The lamp holder 22 is provided with a containing tank 221 to accommodate and cover the lamp cap 1. An interior of the lamp holder 22 is provided with the fastening parts 25 which correspond with the latching parts 15 of the lamp cap 1. In the present embodiment, the fastening parts 25 are L-shaped locking slots 251 and there are also three L-shaped locking slots 251. In addition, openings of the L-shaped locking slots 251, two large and one small, correspond with the latching parts 15, such that the latching parts 15 of the lamp cap 1 can be latched and fixed with the lamp holder 22 through the L-shaped locking slots 251. The lamp holder 22 is provided with connection contacts 26 which correspond with the electric contacts 13 of the lamp cap 1. The aforementioned connection contacts 26 are elastic and arc-shaped units. Moreover, there are three connection contacts in the present embodiment, including a power supply contact 261, a grounding contact 262 and a voltage detection contact 263 by functions. The power supply contact 261 provides the lamp cap 1 with a voltage required for operation, the grounding contact 262 fits with the power supply contact 261 to form a circuit loop, and the voltage detection contact 263 can determine voltage values required by various light sources of the lamp caps 1, and automatically adjust an output voltage, thereby allowing different lamp caps 1 to be replaced freely and to operate normally. Besides, the other function of the voltage detection contact 263 is that if the lamp holder 22 is not provided with any lamp cap 1, then the voltage value will be decreased automatically, which prevents the contacts from generating heat by short-circuiting to cause danger.

A top and a bottom of the lamp holder 2 are provided respectively with more than one heat dissipation hole 27 to dissipate heat generated by the lamp cap 1 or the lamp holder 22.

When assembling for use, as the latching parts 15 and the fastening parts 25 are all two large and one small structures, a user needs to align the lamp cap 1 first that the lamp cap 1 can be inserted into the lamp holder 22, in order to prevent the electric contacts 13 and the connection contacts 26 from being short-circuited if the user inserts in a wrong direction to damage the product. After the lamp cap 1 has been aligned and inserted, the rectangular strips 151 of the latching parts 15 of the lamp cap 1 will be inserted into the L-shaped locking slots 251 of the fastening parts 25 of the lamp body 2 and the lamp cap 1 is rotated clockwise, then the lamp cap 1 will be connected on the lamp holder 22. At this time, as the electric contacts 13 of the lamp cap 1 and the connection contacts 26 of the lamp holder 22 are all elastic and arc-shaped units, when the lamp cap 1 is to be latched with the lamp holder 22, the elastic and arc-shaped units of the electric contacts 13 of the lamp cap 1 will climb and cross over the elastic and arc-shaped units of the connection contacts 26. Through mutual engagement of the latching parts 15 of the lamp cap 1, the fastening parts 25 of the lamp holder 22 and the exposed electric contacts 13 and connection contacts 26, the lamp cap 1 can not only be stably and electrically connected, but be easily dismantled and replaced. In addition, through the control switch 23 on the handheld part 21, the lamp-set can be turned on and turned off.

When the user is to dismantle and replace the lamp cap 1, he or she can operate oppositely that the lamp cap 1 can be separated from the lamp body 2. Accordingly, it is convenient in dismantling and assembling the lamp cap 1 and the lamp body 2, thereby reducing a cost of usage and a cost of procurement.

It is of course to be understood that the embodiments described herein is merely illustrative of the principles of the invention and that a wide variety of modifications thereto may be effected by persons skilled in the art without departing from the spirit and scope of the invention as set forth in the following claims.

What is claimed is:

1. A lamp-set structure comprising:
   a lamp cap, an interior of the lamp cap is accommodated with more than one illuminating element, the illuminating elements being electrically connected with a circuit board, the other end of the circuit board being provided with more than one electric contact, the electric contacts being elastic and arc-shaped units and exposed at a bottom of the lamp cap, peripheries of the lamp cap being provided with more than one latching part to be engaged and connected with fastening parts of a lamp body;
   the lamp body which includes a handheld part and a lamp holder, the handheld part being provided with a control switch, the lamp holder being a containing tank, an interior of the containing tank being provided with the fastening parts corresponding with the latching parts of the lamp cap, an interior of the lamp holder being provided with connection contacts corresponding with the electric contacts of the lamp cap, the connection contacts being elastic and arc-shaped units and the lamp body being provided with a power cord to be electrically connected with the connection contacts.

2. The lamp-set structure according to claim 1, wherein the illuminating element is an LED (Light Emitting Diode).

3. The lamp-set structure according to claim 1, wherein a bottom of the lamp cap is provided with more than one heat dissipation hole.

4. The lamp-set structure according to claim 1, wherein the latching parts are rectangular strips, the fastening parts are L-shaped locking slots, and when the rectangular strips of the latching parts of the lamp cap are inserted into the L-shaped locking slots of the fastening parts of the lamp body and the lamp cap is rotated clockwise, the lamp cap is stably connected on the lamp holder.

5. The lamp-set structure according to claim 1, wherein the handheld part is an ergonomic structure.

6. The lamp-set structure according to claim 1, wherein a top and a bottom of the lamp holder are provided respectively with more than one heat dissipation hole.

7. The lamp-set structure according to claim 1, wherein all the latching parts of the lamp cap and the fastening parts of the lamp body are two large and one small structures, with each latching part corresponding with each fastening part.

8. The lamp-set structure according to claim 1, wherein there are three contacts, including a power supply contact, a grounding contact and a voltage detection contact, respectively.

9. The lamp-set structure according to claim 8, wherein the power supply contact provides the lamp cap with a voltage required for operation.

10. The lamp-set structure according to claim 8, wherein the grounding contact fits with the power supply contact to form a circuit loop.

11. The lamp-set structure according to claim 8, wherein the voltage detection contact determines voltage values required by various light sources of the lamp caps and automatically adjusts an output voltage.

12. The lamp-set structure according to claim 8, wherein when the lamp holder is not provided with any lamp cap, the voltage detection contact automatically decreases the voltage value, preventing the contact from generating heat by short-circuiting to cause danger.

13. A lamp-set structure comprising:
a lamp cap, an interior of the lamp cap is accommodated with more than one illuminating element, the illuminating elements being electrically connected with a circuit board, the other end of the circuit board being provided with three electric contacts exposed at a bottom of the lamp cap, peripheries of the lamp cap being provided with more than one latching part to be engaged and connected with fastening parts of a lamp body;
the lamp body which includes a handheld part and a lamp holder, the handheld part being provided with a control switch, the lamp holder being a containing tank, an interior of the containing tank being provided with the fastening parts corresponding with the latching parts of the lamp cap, an interior of the lamp holder being provided with a power supply contact, a grounding contact and a voltage detection contact corresponding with the electric contacts of the lamp cap, the power supply contact providing the lamp cap with a voltage required for operation, the grounding contact fitting with the power supply contact to form a circuit loop, the voltage detection contact determining voltage values required by various light sources of the lamp caps, automatically adjusting an output voltage and automatically decreasing the voltage value when the lamp holder is not provided with any lamp cap, to prevent the contact from generating heating by short-circuiting to cause danger; on the other hand, the lamp body being provided with a power cord to be electrically connected with the connection contacts.

14. The lamp-set structure according to claim 13, wherein the electric contact is an elastic and arc-shaped unit.

15. The lamp-set structure according to claim 13, wherein the power supply contact, the grounding contact and the voltage detection contact are elastic and arc-shaped units.

16. The lamp-set structure according to claim 13, wherein the illuminating element is an LED.

17. The lamp-set structure according to claim 13, wherein the latching parts are rectangular strips, the fastening parts are L-shaped locking slots, and when the rectangular strips of the latching parts of the lamp cap are inserted into the L-shaped locking slots of the fastening parts of the lamp body and the lamp cap is rotated clockwise, the lamp cap is stably connected on the lamp holder.

18. The lamp-set structure according to claim 13, wherein the latching parts of the lamp cap and the fastening parts of the lamp body are two large and one small structures, with each latching part corresponding with each fastening part.

* * * * *